United States Patent [19]

Lee

[11] Patent Number: 4,506,368

[45] Date of Patent: Mar. 19, 1985

[54] DYE LASERS USING 2-(4-PYRIDYL)-5-ARYLOXAZOLES AND QUATERNARY SALTS OF THESE COMPOUNDS

[75] Inventor: Lester A. Lee, Oxon Hill, Md.

[73] Assignee: The United States of America as represented by the Secretary of the Navy, Washington, D.C.

[21] Appl. No.: 155,248

[22] Filed: Jun. 2, 1980

[51] Int. Cl.$^3$ ............... C07D 413/04; H01S 3/20
[52] U.S. Cl. .................. 372/53; 252/301.17; 546/275; 548/235
[58] Field of Search ............ 372/53; 252/301.16, 252/301.17, 301.26, 301.28; 546/275; 548/235

[56] References Cited

PUBLICATIONS

Lee and Robb, "Water Soluble Blue-Green Lasing Dyes . . . ", IEEE J. of Quantum Electronics, vol. QE 16, No. 7, Jul. 1980, pp. 777-784.

Lee et al., IEEE/OSA Conf. Laser Engineering and Applns. (1979 CLEA), May 29, 1979, absts. of post--deadline papers p. 5.

Ott et al., Oxazole Quaternary Salts, J. American Chemical Society, vol. 78, pp. 1941-1944 (May 1956).

*Primary Examiner*—William D. Larkins
*Attorney, Agent, or Firm*—R. S. Sciascia; A. L. Branning; R. D. Johnson

[57] ABSTRACT

2-(4-pyridyl)-5-aryloxazoles and certain quaternary salts of these compounds are useful as visible-wavelength lasing dyes. These dyes are used in solution with non-interferring polar solvents, such as low molecular weight alcohols, $H_2O$, and $D_2O$, to form lasing media useful in dye lasers. Such lasers generally include a reservoir for containing the laser dye solution and a pumping energy source operably coupled therewith for producing stimulated emission of the dye solution.

18 Claims, No Drawings

DYE LASERS USING 2-(4-PYRIDYL)-5-ARYLOXAZOLES AND QUATERNARY SALTS OF THESE COMPOUNDS

BACKGROUND OF THE INVENTION

This invention relates to lasers and more particularly to organic dye lasers.

In recent years, organic dye lasers have become important tools for spectroscopy, photochemistry, and laser isotope separation. These and other applications are discussed by T. W. Hänsch in "Applications of Dye Lasers," chapter 5 of *Dye Lasers,* F. P. Schäfer, ed. (Springer-Verlag, New York & Heidelberg, Berlin 1973). *Dye Lasers* also provides detailed discussions on the principles of dye laser operation and the theory and structure of laser dyes.

Liquid organic dye lasers offer a number of advantages over gas or solid state lasers. One advantage is that a large number of organic lasing dyes are available that cover a broad range of the electromagnetic spectrum (near UV to near IR). Moreover, the dye lasers may be tuned by such means as varying the concentration of dye or replacing one of the reflecting ends of the laser cavity with a diffraction grating. Dye lasers also offer the advantage of being more economical. Finally, the liquid dye lasers will not crack as do solid lasers.

There is considerable interest in the development of high efficiency organic dyes for high energy dye lasers operating in the blue-green spectral region around 480 nm for applications which involve underwater communications, surveillance, viewing, range gating, etc. These laser dyes should show high photochemical stability even when high energy flashlamp excitation is used to stimulate laser emission from the dyes.

Only a small portion of the broad band radiation from flash lamps is absorbed by most state-of-the-art laser dyes. The unabsorbed radiation is lost by thermalization within the optical cavity of the laser. Unfortunately, the refractive indexes of most solvents are sensitive to temperature change. $H_2O$ and $D_2O$ are preferred because of their large heat capacities and small variation of refractive index with temperature changes. Additionally, $H_2O$ and $D_2O$ have good photostabilities and are non-flammable. Therefore, it would be particularly desirable to find photochemically stable, high efficiency laser dyes which are soluble in water.

SUMMARY OF THE INVENTION

Accordingly, one object of this invention is to provide novel dye lasers which lase in the blue-green wavelength region.

Yet another object of this invention is to provide dye lasers using water or heavy water as the solvent.

A further object of this invention is to provide dye lasers which use dyes having good photochemical stability.

Still another object of this invention is to provide organic dye lasers which can be tuned over a relatively broad range of the emission spectrum.

These and other objects of this invention are achieved by providing: a dye laser comprising a laser dye solution and a pumping energy source operably coupled therewith and capable of producing stimulated emission of the dye solution, the dye solution comprising a lasing concentration in a non-interferring solvent of a dye having the following formula

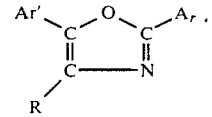

wherein
(A) R is selected from the group consisting of H and $CH_3$;
(B) Ar is selected from the group consisting of

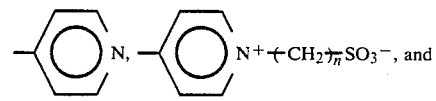

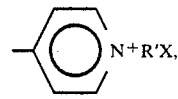

wherein
(1) n is an integer of from 1 through 10;
(2) R' is selected from the group consisting of —H, —D, —$CD_3$, $CD_3CD_2$—, $CF_3CD_2$—, $CF_3CF_2CD_2$—, lower alkyl of from 1 to 10 carbon atoms,

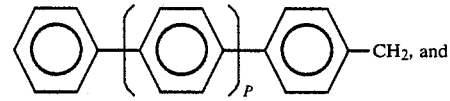

wherein p is 1 or 2 and m is an integer of from 1 through 10; and
(3) $X^-$ is an anion; and
(C) Ar' is selected from the group consisting of

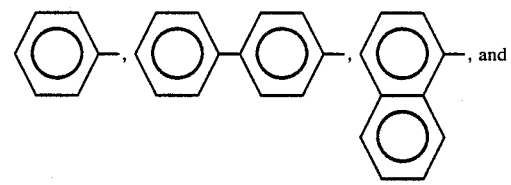

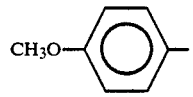

DETAILED DESCRIPTION OF THE PREFERRED EMBODIMENT

The dyes used in the lasers of the present invention can be represented by the formula

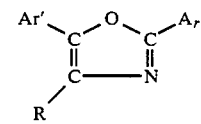

In the formula, R represents either —H or —CH₃. Ar' represents

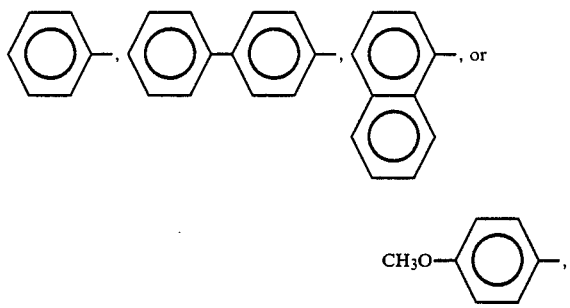

but preferably

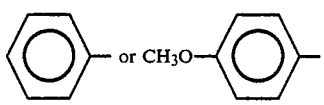

when a quaternary salt having good solubility in H₂O or D₂O is desired.

In the above formula, Ar represents

[I]   [II]

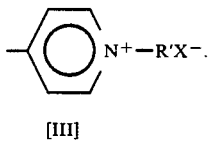

[III]

Compounds having functional groups II and III are preferred because they are quaternary salts and thus more soluble in H₂O and D₂O; quaternary salts containing group III are the more preferred. When Ar represents group II, n is an integer of from 1 to 10.

When Ar is group III, R' is —H, —D, CD₃—, CD₃CD₂—, CF₃CD₂—, CF₃CF₂CD₂—, lower alkyl of from 1 to 10 carbon atoms,

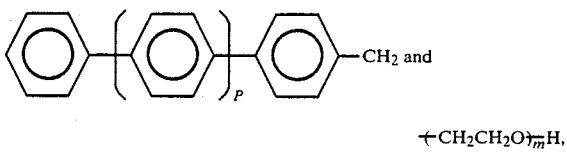

$+CH_2CH_2O\frac{}{m}H$, wherein p is 1 or 2 and m is an integer of from 1 through 10. R' is preferably —H, —D, and lower alkyl of from 1 to 10 carbon atoms. R' is more preferably —H, —D, or —CH₃. The R's preferred are those which produce quaternary salts having good solubility in H₂O and D₂O.

X⁻ in the formula for group III broadly represents any noninterferring anion. Preferably X⁻ is ClO₄⁻, BF₄⁻, Cl⁻, Br⁻, I⁻, HSO₄⁻, CH₃SO₄⁻, CH₃CH₂SO₄⁻, FSO₃⁻, CF₃SO₃⁻, CH₃SO₃⁻, CF₃COO⁻, CCl₃COO⁻, C₆H₅SO₃⁻, P—CH₃C₆H₄SO₃⁻, and H₂NSO₃⁻. More preferably X⁻ is BF₄⁻, Cl⁻, FSO₃⁻, CF₃SO₃⁻, CH₃SO₃⁻, C₆H₅SO₃⁻, P—CH₃C₆H₄SO₃⁻, and H₂NSO₃⁻. Preferably X⁻ is selected to provide a quaternary salt having good solubility in H₂O and D₂O. The anion is the single most important factor in determining this solubility in H₂O and D₂O.

Specific examples of the lasing dyes of the present invention include:

2-(4-pyridyl)-5-phenyloxazole (4PyPO),

4-[2-(5-phenyloxazolyl)]pyridinium perchlorate (4PyPO—HClO₄),

4-[2-(5-phenyloxazolyl)]pyridinium p-toluenesulfonate (4PyPO—HPTS).

4-[2-(5-phenyloxazolyl)]pyridinium hydrochloride (4PyPO—HCl),

4-[2-(5-phenyloxazolyl)]-1-methylpyridinium p-toluenesulfonate (4PyPO—MePTS), 2-(4-pyridyl)-5-p-methoxyphenyloxazole (4PyMPO), 4-[2-(5-p-methoxyphenyloxazolyl)]pyridinium perchlorate (4PyMPO—HClO₄), 4-[2-(5-p-methoxyphenyloxazolyl)]pyridinium p-toluenesulfonate (4PyMPO—HPTS), 4-[2-(5-p-methoxyphenyloxazolyl)]pyridinium hydrochloride (4PyMPO—HCl), and 4-[(2-(5-p-methoxyphenyloxazolyl)]-1-methylpyridinium p-toluenesulfonate (4PyMPO—MePTS).

Any non-interferring solvent (i.e., one that doesn't inhibit stimulated emission) may be used in the laser. Water, deuterium oxide, ethanol, methanol, acetonitrile, and dimethylsulfoxide are examples of suitable solvents. Water and deuterium oxide are the preferred solvents because of their high specific heat coefficients, good photochemical stabilities, and small variation of refractive index with temperature changes. Obviously, the solubility of the dye is a critical factor in selecting a solvent.

A concentration of from $10^{-1}M$ to $10^{-5}M$ of laser dye in solvent is used. A dye concentration of from $10^{-2}M$ to $10^{-4}M$ is preferred because it results in a larger energy output.

Conventional liquid laser apparatus, such as that described by Sorokin et al., IBM Journal, V. 11, p. 148 (1967), may be used with the lasing media of the present invention. The examples of the present disclosure provide specific illustrations of lasers which may be used.

The lasing dyes used in the present invention have high photochemical stability. Moreover, the chemical decomposition products may be separated by physical means from the dyes. Thus, it is possible to circulate the lasing dye solution, remove the decomposition products, and replenish the dye in one continuous process.

The general nature of the invention having been set forth, the following examples are presented as specific illustrations thereof. It will be understood that the invention is not limited to these specific examples but is susceptible to various modifications that will be recognized by one of ordinary skill in the art.

EXPERIMENTAL 2-(4-pyridyl)-5-phenyloxazole (4PyPO), 4-[2-(5-phenyloxazolyl)]-1-methylpyridinium p-toluenesulfonate (4PyPO—MePTS) and 4-[2-(5-phenyloxazolyl)]pyridinium hydrochloride (4PyPO—HCl) were synthesized from α-aminoacetophenone hydrochloride (Aldrich Chemical Company, Inc.) by procedures reported by D. G. Ott, F. N. Hayes, and V. N. Kerr, "Oxazole Quaternary Salts," *J. Amer. Chem. Soc.*, 78, (1956) pp. 1941-4, herein incorporated by reference.

EXAMPLE 1

Synthesis of 2-(4-pyridyl)-5-phenyloxazole

Isonicotinic acid was refluxed with an excess of thionyl chloride to produce isonicotinic acid chloride. After the excess thionyl chloride was removed, the crude isonicotinic acid (4-pyridinecarboxylic acid) chloride was dissolved in pyridine and an equal number of moles of commercially available (from Aldrich Chemical Co., Inc.) of α-aminoacetophenone hydrochloride was added slowly with mixing. The mixture was then heated on a boiling water bath for 2 hours and then drowned in water to precipitate the product α-isonicotinamidoacetophenone, which was then recrystallized from hexane. Finally, the α-isonicotinamidoacetophenone was refluxed in a mixture of acetic anhydride (40 parts) and 90% phosphoric acid (3 parts) to form 2-(4-pyridyl)-5-phenyloxazole (4PyPO). By starting with 2-pyridinecarboxylic acid or 3-pyridinecarboxylic acid, the above method may be used to produce 2-(2-pyridyl)-5-phenyloxazole (2PyPO) or 2-(3-pyridyl)-5-phenyloxazole (3PyPO), respectively.

Because of the high reactivity of the non-bonding electrons on the pyridyl nitrogen atom, 2PyPO, 3PyPO, and 4PyPO are capable of undergoing hundreds of known reactions for pyridine derivatives [see *Pyridine and its Derivatives*, Erwin Klingsberg, Ed., Parts I–IV, Interscience Publishers, Inc., New York (1960) for examples].

Conventional techniques were used to convert the 4PyPO to its quaternary salts used in the examples 4 through 9.

EXAMPLE 2

Synthesis of p-methoxyphenylammonium chloride

A solution of 98% pure α-bromo-p-methoxyacetophenone (obtained commercially from Aldrich Chemical Co., Inc,.) (200 g. ×0.98=196 g., 0.86 moles) in chloroform (300 ml) was added dropwise to a stirred mixture of hexamethylene tetramine (119.95 g., 0.86 moles) in 600 ml. of chloroform. The mixture immediately warmed to 40° C. and the product began to precipitate. The reaction mixture was allowed to stir for 2 hours, filtered and washed with chloroform (600 ml) and air dryed giving a beige colored methylene tetramine quaternary salt (314.23 g, 98.95 percent yield) m.p. 168°–171° C.

The hexamethylene tetramine quaternary salt (40.00 g., 0.108 moles) was stirred in ethanol (425 ml) and concentrated hydrochloric acid (40 ml). The reaction mixture was heated and stirred between 50°–60° C. for 45 minutes and then filtered hot. The white residue (NH$_4$Cl) 10.75 g. was washed with 100 ml of ether (twice). The ethereal washings were allowed to mix with the filtrate, thus precipitating out the main product which was aided by cooling with an ice bath. The product was filtered and washed 3 times with 25 ml ether and dried under vacuum giving 19.00 g. (yield 87%) of p-methoxyphenacylammonium chloride, m.p. 178°–180° C. The process was scaled up and 88.03 g (yield 62%) p-methoxyphenacylammonium chloride, m.p. 178°–180° C. was produced.

EXAMPLE 3

Synthesis of 2-(4-pyridyl)-5-p-methoxyphenyloxazole

Isonicotinic acid (24.93 g., 0.0938 mole) and thionyl chloride (50 ml) was refluxed for 1 hour. The crude acid chloride which remained after removal of excess thionyl chloride at diminished pressure was dissolved in dry pyridine (200 ml) and p-methoxy phenacylammonium chloride (19.00 g, 0.938 mole) was added portion wise to the stirred solution. During the addition, an exotherm occurred which raised the temperature of the stirred mixture to 40° C. After the addition was completed, the reaction mixture was heated and stirred on a boiling water bath for 2 hours and then poured into ice-water to precipitate the product. The solid was collected and dried under reduced pressure to give 12.07 g. (yield 48%) of α-isonicotinamido-p-methoxyacetophenone m.p. 227°–230° C. (with decomposition).

α-isonicotinamido-p-methoxyacetophenone (11.5 g., 0.043 mole) was added portion-wise to a stirred solution of 200 ml of acetic anhydride and 15 ml of 90% phosphoric acid; during the addition an exotherm raised the reaction temperature to 40° C. After the addition was complete the reaction mixture was stirred and refluxed for 2 hours. After cooling, the supernatant liquid was decanted from the viscous precipitate, which was crystallized by titration with 350 ml of 1% aqueous sodium hydroxide. The yellow solid was filtered, washed with distilled water (200 ml), and dried in vacuo yielding 7.76 g. (yield 72%) of 2-(4-pyridyl)-5-p-methoxyphenyloxazole, m.p. 105°–107° C.

By starting with 2-pyridinecarboxylic acid or 3-pyridinecarboxylic acid the above method may be used to produce 2-(2-pyridyl)-5-p-methoxyphenyloxazole (2PyMPO) or 2-(3-pyridyl)-5-p-methoxyphenyloxazole (3PyMPO), respectively.

Because of the high reactivity of the non-bonding electrons on the pyridyl nitrogen atom, 2PyMPO, 3PyMPO, and 4PyMPO are capable of undergoing hundreds of know reactions for pyridine derivatives [see *Pyridine and its Derivatives*, Erwin Klingsberg, Ed., Parts I–IV, Interscience Publishers, Inc., New York (1960)]. Conventional techniques were used to convert the 4PyMPO to its quaternary salts used in the following examples.

In Tables I and II, absorption spectra, including that taken from the literature (OTT et al.), were obtained using $10^{-4}$ solutions. Uncorrected fluorescence spectra were obtained using $10^{-4}$M solutions (10 mm path length) on a Perkin-Elmer MPF-2A Spectrophotometer.

EXAMPLE 4

Solutions of $1\times10^{-3}$M 2-(4-pyridyl)-5-phenyloxazole in dioxane and in absolute ethanol were each pumped with an AVCO C950 pulsed nitrogen gas laser at 3371 Å in a transverse configuration where the rectangular nitrogen laser beam was focused to a line within the magnetically stirred dye cell (1 cm). The pumping laser was capable of 100 kw peak power in a 10 ns pulse duration and can be pulsed at rates as high as 100 pps. The output mirror of the optical cavity was an uncoated quartz flat and the "high reflectivity" end was a broad band reflector. The output of the dye laser was monitored with an EG & G photodiode (SGD-040A) and the wavelength was measured with a Jarrel-Ash ¼ meter monochromator. The lasing wavelength was 3830 Å for 4PyPO in dioxane and 3950–4020 Å in absolute ethanol. This data is shown in Table 1. Also included in Table 1 is data from the literature.

TABLE I

Spectral Characteristics of Laser Dyes and Laser Dye Candidates

| Compound | $\lambda^*_{abs}$ (nm) | $\epsilon$ ($10^{-4}$ lmole$^{-1}$cm$^{-1}$) | $\lambda^{max**}_{fl}$ (nm) | $\lambda^{***}_{las}$ (nm) |
|---|---|---|---|---|
| PPO | 303 | 3.04 | 365 | 361–383 |
|  | 223 | 2.04 |  |  |
| 3PyPO | 320 | 2.42 | 370 |  |
|  | 307 | 2.54 |  |  |
| 2PyPO | 322 | 2.90 | 378 |  |
|  | 310 | 2.64 |  |  |
|  | 224 (sh) | 1.10 |  |  |
| 4PyPO | 322 | 2.62 | 380 | 383(weak) |
|  | 307 | 2.52 |  | 395–402**** |
|  | 224 (sh) | 1.35 |  |  |

\*Cyclohexane
\*\*Toluene
\*\*\*1,4-Dioxane
\*\*\*\*Ethanol
sh shoulder

Dyes were pumped with an AVCO pulsed nitrogen laser at 337.1 nm (100 Kw peak Power). Absorption and fluorescence spectral data is reported by D. G. Ott, F. N. Hayes, E. Hansbury and V. N. Kerr, "Liquid Scintillators V. Absorption and Fluorescence Spectral of 2,5-Diaryloxazoles and Related Compounds", *J. Amer. Chem. Soc.* 79, 5448 (1957). Lasing spectral data for PPO is reported by M. Maeda and Y. Miyazoe, "Efficient Ultraviolet Organic Liquid Laser Pumped by a High Power Nitrogen Laser", *Japan. J. Appl. Phys.*, 13, 827 (1974).

EXAMPLE 5

The procedure used in example 4 was used to test solutions of $1\times 10^{-3}$M 4-[2-(5-phenyloxazolyl)]-1-pyridinium hydrochloride (4PyPO—HCl), 4-[2-(5-phenyloxazolyl)]-1-methylpyridinium p-toluenesulfonate (4PyPO—MePTS), and Eastman Kodak grade Coumarin 175 in deionized water. The lasing wavelengths were 5040 Å for 4PyPO—HCl (at pH2), 5060 Å for 4PyPO—MePTS, and 3570 Å for coumarin 175. These results are listed in Table II in nm.

TABLE II

Spectral Characteristics of Water Soluble Laser Dyes and Laser Dye Candidates

| Compound* | $\lambda_{abs}$ (nm) | ($10^{-4}$ lmole$^{-1}$cm$^{-1}$) | $\lambda^{max}_{fl}$ (nm) | Stokes shift $\lambda$ (nm) | $\lambda^{max}_{las}$ |
|---|---|---|---|---|---|
| 3PyPO—MePTS | 326 | 1.73 | — | — | — |
|  | 256 | 1.31 |  |  |  |
| 2PyPO—MePTS | 360 | 2.22 | — | — | — |
|  | 249 | 1.25 |  |  |  |
| 4PyPO—MePTS | 371 | 2.19 | 470 | 99 | 506 |
|  | 248 | 1.40 |  |  |  |
| 4PyPO—HCl (pH2) | 364 | 2.21 | 470 | 106 | 504 |
|  | 244 | 1.36 |  |  |  |
| Coumarin 175 | 353 | 1.61 | 439 | 86 | 457 |

\*Water (solvent)
Dyes were pumped with an AVCO C950 pulsed nitrogen laser at 337.1nm (100 kw peak power).
Absorption spectral data for aryloxazolyl pyridinium salts reported by D. G. Ott, F. N. Hayes and V. N. Kerr, "Oxazole Quaternary Salts", J. Amer. Chem. Soc., 78, 1941 (1956).

EXAMPLE 6

The tuning ranges for Coumarin 175, 4-[2-(5-phenyloxazolyl)]-1-methylpyridinium p-toluenesulfonate (4PyPO-MePTS), and 4-[2-(5-p-methoxyphenyloxazolyl)]-1-methylpyridinium p-toluenesulfonate (4PyMPO—MePTS) were determined using either $1\times 10^{-3}$M or $2\times 10^{-3}$M solutions in water. The dye laser of examples 4 and 5 was modified by replacing the "high reflectivity" mirror in the optical cavity with a diffraction grating. As in Examples 4 and 5, the output of the pumping laser was at 3371 Å in the ultraviolet. Coumarin 175, 4PyPO—MePTS, and 4PyMPO—MePTS showed broad tuning ranges of 429–470 nm, 470–549 nm, and 547–634 nm respectively. The results are listed in Table III.

TABLE III

Tuning Ability of Water Soluble Lasing Dyes in $H_2O$

| Dye | Tuning Range (nm)* |
|---|---|
| Coumarin 175 ($1 \times 10^{-3}$ M) | 476–429 |
| 4PyPO—MePTS ($1 \times 10^{-3}$ M) | 549–470 |
| 4PyMPO—MePTS ($2 \times 10^{-3}$ M) | 634–547 |

\*Tuning range of laser dye with a diffraction grating when pumped with an AVCO C950 pulsed nitrogen laser at 337.1 nm (100 kw peak power).

EXAMPLE 7

The flashlamp pumped dye laser used in this experiment was the same one described by E. J. Schimitschek, J. A. Trias, P. R. Hammond and R. L. Atkins "Laser Performance and Stability of Fluorinated Coumarin Dyes", *Opt. Commun.*, 11, 352 (1974). About 0.2 ml of the particular dye solution contained in a quartz capillary cell was repetitively exposed to the light of a linear flashlamp, energized by a low inductance capacitor charged to 5 Joules. The light from the flashlamp was passed through an AMERSIL type M-68 ozone free quartz sleeve with a cut-off wavelength at 220 nm, before it reached the dye solution. The elliptical laser head, consisting of an optically finished aluminized quartz sleeve, was completely filled with water. The repetition rate was kept at 0.5 Hz to minimize heating of the stationary dye solution. Spherical mirrors of 12.5 cm radius of curvature in direct contact with the dye solution and reflectivities of 99% and 80%, respectively, formed the resonator.

For each dye solution, the initial peak output power and the number of shots to the 50% decline point of that power was measured. The untuned lasing wavelength was recorded at the beginning of each test with a Beck Reversion Spectroscope. $7.5 \times 10^{-4}$M solutions of Coumarin 175, 4-[2-(5-phenyloxazolyl)]-1-methylpyridinium p-toluenesulfonate (4PyPO—MePST), 4-[2-(5-phenyloxazolyl)]-1-pyridinium hydrochloride (4PyPO—HCl), and 4-[2-(5-p-methoxyphenyloxazolyl)]-1-methylpyridinium p-toluenesulfonate (4PyM- PO—MePTS) in deionized water, and also C8F in absolute ethanol. The energy input into the flashlamp was 5J.

The results given in Table IV show that 4PyPO—MePTS and 4PyPO—HCl exhibit more than thirty times the life of coumarin 175 to one-half power. C8F, which is one of the most photochemically stable laser dyes reported to date (by Schmitschek et al., supra), exhibited 124 times the life of coumarin 175 to one-half power. Unfortunately, C8F does not lase in pure water because of limited solubility and low fluorescence quantum efficiency.

TABLE IV

LASER DYE PERFORMANCE AT 5J ENERGY INPUT INTO FLASHLAMP

| Dye ($7.5 \times 10^{-4}$ M) | Solvent | Wavelength Untuned (nm) | Initial Peak Output Power (kw) | Relative Number of Laser Shots to 50% Decline of initial output |
|---|---|---|---|---|
| C8F | EtOH | 522 | 8.0 | 990 |
| 4PyPO—MePTS | H$_2$O | 506 | 2.3 | 281 |
| 4PyPO—HCl | H$_2$O (pH2) | 504 | 4.8 | 264 |
| Coumarin 175* | H$_2$O | 462 | 4.5 | 8 |
| 4PyMPO—MePTS | H$_2$O | 567 | 0.5 | 160 |

*Eastman Kodak Grade

EXAMPLE 9

Lasing data was also obtained for 2-(4-pyridyl)-5-p-methoxyphenyoxazole and some of its pyridinium salts. This is presented in Table V.

TABLE V

Lasing Data for 2-(4-Pyridyl)-5-p-Methoxyphenyloxazole and its Pyridinium Salts

| Compound* ($2 \times 10^{-3}$ M) | $\lambda_{las}^{max}$ (nm) | Solvent |
|---|---|---|
| 4PyMPO | 443 | ethanol |
| 4PyMPO—HClO$_4$ | 568 | ethanol |
| 4PyMPO—HPTS | 563 | ethanol |
| 4PyMPO—HCl | 562 | ethanol |
| 4PyMPO—MePTS | 586 | H$_2$O |

Dyes were pumped with an AVCO C950 pulsed nitrogen laser at 337.1 nm (100 kw peak power).

Obviously numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. 4-[2-(5-p-methoxyphenyloxazolyl)]pyridinium p-toluenesulfonate.
2. 4-[2-(5-p-methoxyphenyloxazolyl)]pyridinium hydrochloride.
3. 4-[2-(5-p-methoxyphenyloxazolyl)]-1-methylpyridinium p-toluenesulfonate.
4. A dye laser comprising a laser dye solution and a pumping energy source operably coupled therewith and capable of producing stimulated emission of the dye solution, the dye solution comprising a lasing concentration in a non-interferring solvent selected from the group consisting of H$_2$O, D$_2$O, and mixtures thereof of a dye having the following formula

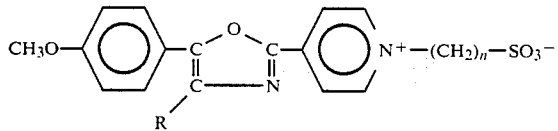

wherein n is an integer of from 1 through 10 and R is selected from the group consisting of —H and —CH$_3$.

5. A dye laser comprising a laser dye solution and a pumping energy source operably coupled therewith and capable of producing stimulated emission of the dye solution, the dye solution comprising a lasing concentration in a non-interfering solvent selected from the group consisting of H$_2$O, D$_2$O, and mixtures thereof of a dye which is a quaternary salt selected from the group consisting of 4-[2-(5-p-methoxyphenyloxazolyl)]pyridinium p-toluenesulfonate,
4-[2-(5-p-methoxyphenyloxazolyl)]pyridinium hydrochloride, and
4-[2-(5-p-methoxyphenyloxazolyl)]-1-methylpyridinium p-toluenesulfonate.

6. The dye laser of claim 5 wherein the dye is the quaternary salt 4-[2-(5-p-methoxyphenyloxazolyl)]pyridinium p-toluenesulfonate.

7. The dye laser of claim 5 wherein the dye is the quaternary salt 4-[2-(5-p-methoxyphenyloxazolyl)]pyridinium hydrochloride.

8. The dye laser of claim 5 wherein the dye is the quaternary salt 4-[2-(5-p-methoxyphenyloxazolyl)]-1-methylpyridinium p-toluenesulfonate.

9. A method of producing coherent laser emission in the operation of a dye laser comprising the steps of optically pumping a dye solution to produce a population inversion in the solution and stimulating an emission of a beam of radiation therefrom, the solution containing about $10^{-5}$ to about $10^{-1}$ molar concentration of a lasing dye in a non-interfering solvent selected from the group consisting of H$_2$O, D$_2$O, and mixtures thereof, said dye having a formula as follows:

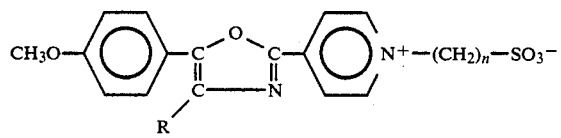

wherein n is an integer of from 1 through 10 and R is selected from the group consisting of —H and —CH$_3$.

10. The method of claim 9 wherein the solution contains from $10^{-4}$ to $10^{-2}$ molar concentration of lasing dye.

11. A method of producing coherent laser emission in the operation of a dye laser comprising the steps of optically pumping a dye solution to produce a population inversion in the solution and stimulating an emission of a beam of radiation therefrom, the solution containing about $10^{-5}$ to about $10^{-1}$ molar concentration of a lasing dye in a non-interfering solvent selected from the group consisting of $H_2O$, $D_2$, and mixtures thereof, said dye being a quaternary salt selected from the group consisting of 4-[2-(5-p-methoxyphenyloxazolyl)]pyridinium p-toluenesulfonate, 4-[2-(5-p-methoxyphenyloxazolyl)]pyridinium hydrochloride, and 4-[2-(5-p-methoxyphenyloxazolyl)]-1-methylpyridinium p-toluenesulfonate.

12. A method according to claim 11 wherein the solution contains from $10^{-4}$ to $10^{-2}$ molar concentration of a lasing dye.

13. The method of claim 11 wherein the dye is the quaternary salt 4-[2-(5-p-methoxyphenyloxazolyl)]pyridinium p-toluenesulfonate.

14. The method of claim 13 wherein the solution contains from $10^{-4}$ to $10^{-2}$ molar concentration of the lasing dye.

15. The method of claim 11 wherein the dye is the quaternary salt 4-[2-(5-p-methoxyphenyloxazolyl)]pyridinium hydrochloride.

16. The method of claim 15 wherein the solution contains from $10^{-4}$ to $10^{-2}$ molar concentration of the lasing dye.

17. The method of claim 11 wherein the dye is the quaternary salt 4-[2-(5-p-methoxyphenyloxazolyl)]-1-methylpyridinium p-toluenesulfonate.

18. The method of claim 17 wherein the solution contains from $10^{-4}$ to $10^2$ molar concentration of the lasing dye.

* * * * *